(12) United States Patent
Hirai et al.

(10) Patent No.: US 6,395,773 B1
(45) Date of Patent: May 28, 2002

(54) ANTI-DRUG RESISTANT STRAIN AGENTS AND ANTICHLAMYDIA AGENTS

(75) Inventors: Keiichi Hirai, Ishikawa; Kumiko Nagata, Hyogo; Junko Koyama, Hyogo; Toshio Kishimoto, Okayama, all of (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/856,895

(22) PCT Filed: Sep. 28, 2000

(86) PCT No.: PCT/JP00/06710

§ 371 (c)(1),
(2), (4) Date: Jul. 23, 2001

(87) PCT Pub. No.: WO01/23372

PCT Pub. Date: Apr. 5, 2001

(30) Foreign Application Priority Data

Sep. 29, 1999 (JP) ............................................ 11-277335

(51) Int. Cl.$^7$ ...................... A61K 31/343; C07D 307/77
(52) U.S. Cl. ........................................ 514/468; 549/458
(58) Field of Search ........................... 549/458; 514/468

(56) References Cited

FOREIGN PATENT DOCUMENTS

JP          9-249560          9/1997

Primary Examiner—Ba K. Trinh
(74) Attorney, Agent, or Firm—Wenderoth, Lind & Ponack, L.L.P.

(57) ABSTRACT

In order to provide antibacterial agents for drug-resistant bacteria and anti-Chlamydia agents, the furanonaphthoquinone derivative represented by the following formula (1):

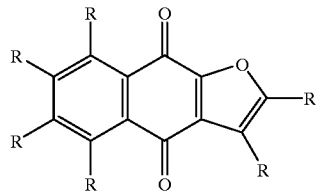

(1)

wherein each R may be the same or different, representing any one of the following (a) to (e):

—R'  (a)

—OR'  (b)

—CR'  (c)
  ‖
  O

—OCR'  (d)
  ‖
  O

—SR'  (e)

(wherein R' is a hydrogen atom, alkyl group, hydroxyalkyl group, or alkoxyalkyl group), or two mutually adjacent Rs may be bonded via an oxygen atom to form a heterocyclic ring is used as the effective component.

2 Claims, No Drawings

ANTI-DRUG RESISTANT STRAIN AGENTS AND ANTICHLAMYDIA AGENTS

This application is a 371 of PCT/JP00/06710 dated Sep. 28, 2000.

TECHNICAL FIELD

The invention of the present application relates to antibacterial agents for drug-resistant bacteria and anti-Chlamydia agents. More particularly, the present invention relates to novel antibacterial agents for drug-resistant bacteria and anti-Chlamydia agents, which comprise highly active furanonaphthoquinone derivatives as effective components.

BACKGROUND ART

In recent years, methicillin-resistant *Staphylococcus aureus* (MRSA) has been seriously considered as the causal bacterium of hospital infection. Since this MRSA is a multiple drug resistant bacterium for a variety of antibiotics, there is a limitation to the drugs that may be used effectively as therapeutic agents.

Additionally, at present, no antibacterial agent is known which show a stronger antibiotic activity against MRSA (resistant bacterium) than against MSSA (sensitive bacterium).

Accordingly, the realization of antibacterial agents for drug-resistant bacteria with high antibacterial activity has been strongly desired.

On the other hand, Chlamydia is a spherical bacterium of 0.2 μm in diameter, which is known to be the causal bacterium of parrot fever infected from pet birds (accompanied with fever, headache, and pneumonia), infections caused by sexual intercourse, urethritis, cervicitis, lymphogranuloma venereum, conjunctivitis, pneumonia, etc. In Asia and Africa, trachoma accompanying blindness is raging. In addition, recent studies have found Chlamydia infections, which cause infertility in women and arteriosclerosis.

Although antibiotics such as macrolide derivatives and tetracycline derivatives have been used as therapeutic agents, in practice, the incidence rate is reported to be higher than that of gonorrhea.

Moreover, since recent new drugs have broad spectra, the acquisition of resistance of other bacteria against drugs has become a problem. Therefore, the development of novel highly specific anti-Chlamydia agents of which the action mechanism is different from that of the drugs known so far, is anticipated.

DISCLOSURE OF INVENTION

In this situation, as a means to solve the above-mentioned problem, the invention of the present application provides antibacterial agents for drug-resistant bacteria and anti-Chlamydia agents comprising, as the effective component, the furanonaphthoquinone derivative represented by the following formula (1):

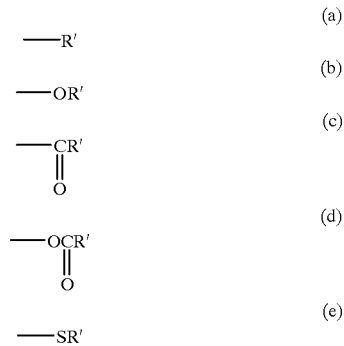

wherein each R may be the same or different representing any one of the following (a) to (e):

$$—R'  \quad (a)$$
$$—OR' \quad (b)$$
$$—\underset{\underset{O}{\|}}{C}R' \quad (c)$$
$$—O\underset{\underset{O}{\|}}{C}R' \quad (d)$$
$$—SR' \quad (e)$$

(wherein R' is a hydrogen atom, alkyl group, hydroxyalkyl group, or alkoxyalkyl group), or two mutually adjacent Rs may be bonded via an oxygen atom to form a heterocyclic ring.

BEST MODE FOR CARRYING OUT THE INVENTION

In the anti-viral agents and antibacterial agents of the present invention described above, wherein furanonaphthoquinone derivatives are used as the effective component, a wide variety of furanonaphthoquinone derivatives may be used. These are exemplified by, for example, 2-methylnaphtho[2,3-b]furan-4,9-dione, 2-acetylnaphtho[2,3-b]furan-4,9-dione, 2-(1-hydroxyethyl)naphtho[2,3-b]furan-4,9-dione, naphtho[2,3-b]furan-4,9-dione, 5(or 8)-hydroxy-2-(1-hydroxyethyl)naphtho[2,3-b]furan-4,9-dione, 5(or 8)-hydroxynaphtho[2,3-b]furan-4,9-dione, 2-methyl-5(or 8)-hydroxy-2-methylnaphtho[2,3-b]furan-4,9-dione, 1,3-dimethylisofuranonaphthoquinone, 2-(acetylethylenacetal)naphtho[2,3-b]furan-4,9-dione, 8-hydroxy-7-methoxynaphtho-[2,3-b]furan-4,9-dione, 3-acetyl-5,8-dimethoxy-2-methylnaphtho[2,3-b]furan-4,9-dione, etc. The furanonaphthoquinone derivatives used in this invention are not limited to these examples, and a variety of embodiments represented by the above formula maybe included. In addition, to the alkyl group, hydroxyalkyl group, and alkoxyalkyl group of the above formula, other substituents such as alkenyl group, cycloalkyl group, cycloalkenyl group, aryl group, halogen atom, amino group, nitro group, cyano group, thiol group, thioether group, carboxyl group, ester group, amide group, sulfonyl group, haloformyl group, heterocyclic group, etc., may optionally be attached, as long as they do not interfere with the activity.

These various compounds may be produced by a variety of known methods of chemical synthesis or by methods such as the extraction of naphthoquinone as natural product from bark, etc.

The mode for carrying out the invention is explained in more detail by the following examples.

EXAMPLES

Reference Example 1

Production of 2-methylnaphtho[2,3-b]furan-4,9-dione (Compound A)

2-Hydroxy-3-(2-propenyl)-1,4-naphthoquinone (150 mg) synthesized from 2-hydroxy-1,4-naphthoquinone and propionaldehyde was refluxed together with DDQ (200 mg) in benzene (20 ml) under stirring. After 2 to 3 hours, the reaction mixture was cooled and filtered, and the filtrate was distilled. The residue was subjected to column chromatography (30 g of silica gel, benzene), and the first yellow fraction obtained gave the desired Compound A (FNQ3) as yellow crystals (35%).

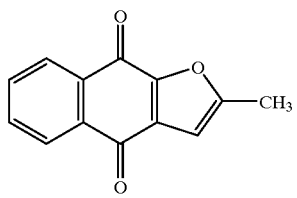

(A)

Reference Example 2

Production of 8-hydroxy-2-methylnaphtho[2,3-b]furan-4,9-dione (Compound B)

Aluminum chloride (2.5 g) and 3-hydroxyphthalic anhydride (1 g) were added to nitrobenzene (5 ml), to which was added 2-acetyl-5-methylfuran (0.7 g), dropwise, and heated at 100° C. overnight.

After the product was extracted with chloroform, nitrobenzene was removed by vacuum distillation; the product was then purified by column chromatography (50 g of silica gel, benzene) to give Compound B (FNQ13) as yellow crystals (<5%).

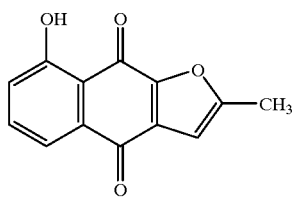

(B)

Example 1

Antibacterial Agent for Drug-Resistant Strain

<A> Materials for Test

*Staphylococcus aureus*

A total of 14 strains of methicillin-resistant *Staphylococcus aureus* (MRSA) in the logarithmic growth phase, including 11 strains clinically isolated at the Hospital of Hyogo College of Medicine and three subcultured strains, were used.

As controls, a total of 12 strains of the similarly isolated methicillin-sensitive *Staphylococcus aureus* (MSSA), including 11 clinical isolates and one subcultured strain, were used.

*Candida albicans*

Six clinical isolates of fluconazole-resistant *Candida albicans* (FRCA) in the logarithmic growth phase, which were isolated at the Hospital of Hyogo College of Medicine, were used.

As controls, five similarly isolated strains of fluconazole-sensitive *Candid albicans* (PSCA) were used.

<B> Test Method

Proliferation Inhibitory Test for *Staphylococcus aureus*

A certain amount of compound B (FNQ13) dissolved in DMSO and diluted with 0.9% sodium chloride-containing phosphate buffer was added onto a Mueller-Hinton agar medium (Difco Co.), and incubated at 37° C. for 24 hours.

The number of the *Staphylococcus aureus* colony occurring on the surface of the agar medium was counted, and the minimum inhibitory concentration (MIC) of the compound, which inhibited growth by 100%, was determined according to the standard method of the Japanese Society of Chemotherapy (Chemotherapy 38; 102–105, 1990).

As a blank, only the phosphate buffer containing DMSO and 0.9% sodium chloride was added.

Proliferation Inhibitory Test for *Candida albicans*

A certain amount of FNQ13 dissolved in DMSO and diluted with 0.9% sodium chloride-containing phosphate buffer was added onto an RPMI-1640 agar medium containing morpholine-propanesulfonic acid, and incubated at 35° C. for 5 days.

The number of the *Candida albicans* colony occurring on the surface of the agar medium was counted, and the minimum inhibitory concentration (MIC) of the compound, which inhibited growth by 100%, was determined according to the standard method of the Japanese Society of Chemotherapy.

<C> Result

The antibacterial activity of Compound B (FNQ13) against MRSA and FRCA are shown in Table 1 and Table 2, respectively.

From Table 1, it was found that the mean MIC of MRSA (resistant strain) was 5.36 μg/ml, and MIC of MSSA (sensitive strain), 11.98 μg/ml, indicating that FNQ13 exhibits a stronger antimicrobial activity against MRSA (resistant strain).

TABLE 1

Antibacterial activity of Compound (FNQ13) against MRSA and MSSA

| Strain | MRSA MIC (μg/ml) | Strain | MSSA MIC (μg/ml) |
|---|---|---|---|
| 1 (Patient) | 6.25 | 1 (Patient) | 25.0 |
| 2 (Patient) | 3.13 | 2 (Patient) | 6.25 |
| 3 (Patient) | 3.13 | 3 (Patient) | 12.5 |
| 4 (Patient) | 12.5 | 4 (Patient) | 12.5 |
| 5 (Patient) | 12.5 | 5 (Patient) | 12.5 |
| 6 (Patient) | 3.13 | 6 (Patient) | 6.25 |
| 7 (Patient) | 6.25 | 7 (Patient) | 6.25 |
| 8 (Patient) | 3.13 | 8 (Patient) | 12.5 |
| 9 (Patient) | 6.25 | 9 (Patient) | 12.5 |
| 10 (Patient) | 3.13 | 10 (Patient) | 12.5 |
| 11 (Patient) | 6.25 | 11 (Patient) | 12.5 |
| 12 (N133) | 1.56 | 12 (1840) | 12.5 |
| 13 (OF4) | 1.56 | | |
| 14 (N295) | 6.25 | | |
| Mean ± standard deviation | 5.36 ± 3.5 | Mean ± standard deviation | 11.98 ± 4.9* |

*p < 0.01

On the other hand, from Table 2, it was shown that FNQ13 exhibits the same degree of antibacterial activity against FRCA (resistant strain) of *Candida albicans* as that against FSCA (sensitive strain).

TABLE 2

Antimicrobacterial Activity of Compound (FNQ13) and
fluconazole against FRCA and FSCA

| | FRCA | | | FSCA | |
|---|---|---|---|---|---|
| Strain | FNQ13 MIC (μg/ml) | FLCZ | Strain | FNQ13 MIC (μg/ml) | FLCZ |
| MCV7 | 2 | 32 | TA | 4 | 0.03 |
| CA383 | 2 | >64 | TIMM1756 | 2 | 0.06 |
| S78941 | 4 | >64 | TIMM1850 | 2 | 0.06 |
| CA8941 | 8 | >64 | TIMM0239 | 2 | 0.13 |
| T77042 | 2 | >64 | 1FO0583 | 4 | 0.03 |
| DUNC136 | 4 | >64 | | | |

FLCZ: fluconazole

Example 2

Drug Resistance Decreasing Effect

<A> Materials for Test

*Staphylococcus aureus*

Methicillin-resistant *Staphylococcus aureus* (MRSA) in the logarithmic growth phase, clinically isolated at the Hospital of Hyogo College of Medicine, were used.

As controls, the similarly isolated strains of methicillin-sensitive *Staphylococcus aureus* (MSSA) were used.

<B> Test Method

Effect on decreasing antibiotic resistance by concomitant use

To HP-plates (Eiken Chemical Co., Ltd.) on which an agar medium containing a variety of antibiotics (Microbiol. Immunol. 41; 703–708, 1997) was set, Compound A (FNQ3) dissolved in DMSO and diluted with 0.9% sodium chloride-containing phosphate buffer was added so that the final concentration is 0.5 μg/ml, and incubated at 37° C. for 24 hours.

The number of the *staphylococcus aureus* colony occurring on the surface of the agar medium was counted, and the minimum inhibitory concentration (MIC) of the compound, which inhibited growth by 100%, was determined according to the standard method of the Japanese Society of Chemotherapy.

The concentration of 0.5 μg/ml of FNQ3 alone used in this test had no influence on the growth of *Staphylococcus aureus*.

As a blank for the concomitant test, only DMSO and the phosphate buffer containing 0.9% sodium chloride was added and used without the concomitant use of FNQ3.

<C> Test Result

The antibacterial activity of Compound A (FNQ3) against MRSA and MSSA are shown in Table 3.

TABLE 3

Effect of concomitant use of compoound (FNQ3) on the antibacterial
activity of various antibiotics against MRSA

| | MIC (μg/ml) | | | |
|---|---|---|---|---|
| | MRSA | | MSSA | |
| Antibiotics | −FNQ3 | +RNQ3* | −FNQ3 | +FNQ3* |
| Ampicillin | 32 | 4 | 32 | 16–32 |
| cefaclor | 64 | 16 | 1 | 1 |
| Cefotiam | 32 | 16–32 | 0.25–0.5 | 0.25 |
| Clarithromycin | 16 | 16 | 0.5 | 0.5–1 |
| Roxithromycin | 16 | 16 | 1 | 1 |
| Levofloxacin | 8 | 4 | 0.25 | 0.25 |
| Minacycline | 8 | 2–4 | 0.25 | 0.25 |
| Vancomycin | 2.5 | 0.6–1.25 | 0.6 | 0.6 |

Table 3 shows that a low concentration of the Compound (0.5 μg/ml) decreases the resistance of MRSA against antibiotics such as ampicillin, cefaclor, levofloxacin, minocycline, vancomycin, etc., from ½ to ¼.

As described above, in recent years, MRSA has become an important causal bacteria of hospital infections. However, as can be seen in Table 3, drugs to be used as therapeutic agents are limited because of its multiple drug resistance against many antibiotics.

Against such bacteria, the above-mentioned compounds of the present invention, represented by formula (1), can inhibit their growth at a relatively low concentration, and the MIC values are lower than those against MSSA (Table 1). In other words, the above-mentioned compounds are rather more sensitive to MRSA.

Furthermore, from Table 3, it was indicated that low concentrations of the above-mentioned compounds enhance the sensitivity of MRSA to antibiotics formerly used against *Staphylococcus aureus*, such as amoxicillin derivatives (ampicillin, etc.).

Since no antibacterial agent more active against MRSA (resistant strain) than against MSSA (sensitive strain) has been known so far, the above-mentioned compounds are anticipated as the effective components in therapeutic agents, such as concomitant drugs comprising antibacterial agents or antibiotics against MRSA. Although the growth inhibition mechanism of the present compound against MRSA has not been clarified at present, it has been found that it differs greatly from that of formerly known antibiotics, in that it involves the generation of active oxygen, which is highly bactericidal, in the bacterial cell membrane.

In addition, as for its toxicity to human cells, it has been reported that the concentration, which causes 100% necrosis in human cancer cells, is about 5 μg/ml, while that for normal human cells is about 20 μg/ml (J. Electron Microsc. 46; 181–187, 1997).

Accordingly, each compound of the present invention, which may be used as the effective component in antibacterial agents against drug-resistant strains, are advantageous in that it exhibits drug efficacy as anti-cancer agent, but shows no toxicity to normal cells and causes no side effects for intravenous or oral administration, at concentrations effective as antibacterial agent (5 μg/ml or less).

Example 3

Anti-Chlamydia Activity

Although diseases possibly caused by chronic infections with Chlamydia, such as the involvement of *C. pneumoniae* in arteriosclerosis, and infertility caused by *C. trachomatis*, etc., are regarded as important, it is considered highly possible that the long-term administration of conventional anti-Chlamydia agents, for the prevention and/or treatment of such diseases, may cause additional problems such as the emergence of resistant strains, and side effects.

Therefore, the screening of new substances, which may be useful as prophylactics or therapeutic agents for chronic diseases caused by Chlamydia, is considered to be meaningful.

<A> Materials for Test

Hence, the furanonaphthoquinone (FNQ) derivative having selective anti-tumor effect and various antibacterial effects, derived from the South American plant, Tecoma ipe Mart, drew the inventor's attention, and its anti-Chlamydia effect was examined, in vitro.

<E> Test Method

As culture cells, HeLa229, McCoy and WI38 were used. As Chlamydia, TW-183 strain and KKpn-1 strain of *C. pneumoniae*, $L_2$ strain, D strain and F strain of *C. trachomatis*, and Cal10 strain of *C. psittaci* were used.

As for FNQ3 and the Compound derived from FNQ3 by replacing the methyl group with —$CH_2OH$ (FNQ19), the MIC was determined according to the standard method of the Japanese Society of Chemotherapy. Additionally, morphometrical observations were performed using an electron microscope.

The results are shown in Table 4 and Table 5.

<C> Test Result

Table 4 and Table 5 show that both FNQ3 and FNQ19 completely inhibit the growth of all tested strains of Chlamydia at a low concentration of 0.25 to 1.0 µg/ml. It was recognized that the MIC value showed a tendency to decrease to approximately ½, when McCoy and WI38 cells were used, as compared to when HeLa229 cells were used.

Further, through the observations by electron microscope, it was also confirmed that the growth was suspended after 18 hours of drug addition, and remained completely inhibited even after 72 hours. Although a detailed mechanism of anti-Chlamydia effect has not been clarified at present, it was confirmed that the FNQ derivatives could be useful as prophylactics or therapeutic agents for diseases caused by chronic infections with Chlamydia.

TABLE 4

Anti-chlamydial activity of FNQ3 (MIC µg/ml)

|  | HeLa229 | McCoy | WI 38 |
|---|---|---|---|
| *C. pneumoniae* |  |  |  |
| TW-183 | 0.6 |  | N.D. |
| KKpn-1 | 0.25 | 0.25 |  |
| *C. trachomatis* |  |  |  |
| $L_2$ | 1.0 | 0.6 | 0.5 |
| D | 1.0 |  |  |
| F | 1.0 |  |  |
| *C. psittaci* |  |  |  |
| Cal 10 | 1.0 | 0.5 | 0.25 |

TABLE 5

Anti-chlamydial activity of FNQ19 (MIC µg/ml)

|  | HeLa229 | WI 38 |
|---|---|---|
| *C. pneumoniae* |  |  |
| KKpn-1 | 0.5 | N.D. |

TABLE 5-continued

Anti-chlamydial activity of FNQ19 (MIC µg/ml)

|  | HeLa229 | WI 38 |
|---|---|---|
| *C. trachomatis* |  |  |
| $L_2$ | 0.25 | 0.25 |
| *C. psittaci* |  |  |
| Cal 10 | 0.25 | 0.25 |

INDUSTRIAL APPLICABILITY

As described in detail above, the invention of the present application provides antibacterial agents for drug resistant strains, which are highly active against methicillin resistant *Staphylococcus aureus* and fluconazole resistant *Candida albicans*, and are able to decrease the resistance of said microorganisms to said antibiotics when used in combination with conventional antibiotics. Further, the present antibacterial agents show little toxicity to human cells.

Additionally, the invention provides highly active anti-Chlamydia agents, as well.

What is claimed is:

1. An antibacterial agent for drug-resistant bacteria comprising, as the effective component, a furanonaphthoquinone derivative represented by the following formula (1):

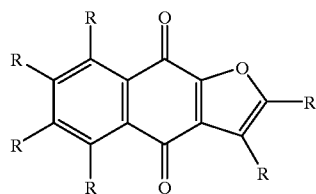

(1)

wherein each R may be the same or different, representing any one of the following (a) to (e):

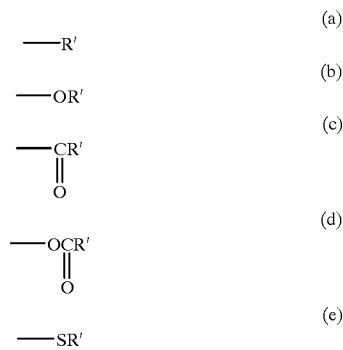

(wherein R' is a hydrogen atom, an alkyl group, a hydroxyalkyl group, or an alkoxyalkyl group), or two mutually adjacent Rs may be bonded via an oxygen atom to form a heterocyclic ring.

2. An anti-Chlamydia agent comprising, as the effective component, a furanonaphthoquinone derivative represented by the following formula (1):

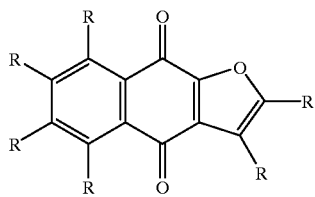
(1)
wherein each R may be the same or different, representing any one of the following (a) to (e):
 (a)
 (b)
 (c)
 (d)
 (e)
(wherein R' is a hydrogen atom, alkyl group, hydroxyalkyl group, or alkoxyalkyl group), or two mutually adjacent Rs may be bonded via an oxygen atom to form a heterocyclic ring.
* * * * *